US00PP10104P

United States Patent [19]

Wain

[11] Patent Number: Plant 10,104

[45] Date of Patent: Nov. 4, 1997

[54] CHRYSANTHEMUM PLANT NAMED 'DARK FASHION TIME'

[75] Inventor: Peter Wain, Hayling Island, United Kingdom

[73] Assignee: Cleangro Ltd., Chichester, United Kingdom

[21] Appl. No.: 664,970

[22] Filed: Jun. 13, 1996

[51] Int. Cl.[6] ..... H01H 5/00

[52] U.S. Cl. ..... Plt./76

[58] Field of Search ..... Plt./76, 80

*Primary Examiner*—Howard J. Locker

*Attorney, Agent, or Firm*—C. A. Whealy

[57] ABSTRACT

A distinct cultivar of Chrysanthemum plant named Dark Fashion Time, characterized by its flat capitulum form; vigorous and tall growth habit; freely branching plant habit; medium decorative-type inflorescences; lavender ray florets; numerous inflorescences per plant; numerous ray florets per inflorescence; and good postproduction longevity.

1 Drawing Sheet

The present invention relates to a new and distinct cultivar of Chrysanthemum plant, botanically known as *Dendranthema grandiflora* and referred to by the cultivar name Dark Fashion Time.

The new cultivar is a spontaneous nutation of the commercial cultivar Fashion Time (U.S. Plant application Ser. No. 08/627,606). The new cultivar was discovered and selected by the inventor in a controlled environment in Havant, Hampshire, United Kingdom, as a single plant among a population of plants of the cultivar Fashion Time. This single plant consistently formed inflorescences having lavender-colored ray florets compared to the pink-colored ray florets of plants of the cultivar Fashion Time.

Asexual reproduction of the new cultivar by terminal cuttings taken at Havant, Hampshire, United Kingdom, has shown that the unique features of this new Chrysanthemum are stable and reproduced true to type in successive generations.

The following traits have been repeatedly observed and are determined to be the unique characteristics of Dark Fashion Time. These characteristics in combination distinguish Dark Fashion Time as a new and distinct cultivar:

1. Flat capitulum form.
2. Vigorous and tall growth habit.
3. Freely branching plant habit.
4. Medium decorative-type inflorescences.
5. Lavender ray florets.
6. Numerous inflorescences per plant.
7. Numerous ray florets per inflorescence.
8. Good postproduction longevity with inflorescences maintaining good substance and color for more than 18 days in an interior environment.

The cultivar Dark Fashion Time has not been observed under all possible environmental conditions. The phenotype may vary somewhat with variations in environment such as temperature, daylength and light intensity, without, however, any variance in genotype.

Plants of the new Chrysanthemum are similar to the mutation parent cultivar Fashion Time in plant habit and growth rate. However in side-by-side comparisons in Oxnard, Calif., under commercial practice, plants of the new Chrysanthemum had ray florets that were lavender in color and ray florets of plants of the cultivar Fashion Time were pink in color. A detailed comparison of these differences appears in Chart A at the end of the specification.

Plants of the new Chrysanthemum are similar to the cultivar Charm (disclosed in U.S. Plant Pat. No. 5,502) in ray floret color. However, in side-by-side comparisons conducted in Oxnard, Calif., under commercial practice, the new Chrysanthemum differed from the cultivar Charm in the following characteristics:

1. Plants of the new Chrysanthemum are taller, are more vigorous, and have longer peduncles than plants of the cultivar Charm.
2. Plants of the new Chrysanthemum are more freely branching than plants of the cultivar Charm.
3. The color of the ray florets on plants of the new Chrysanthemum is slightly darker than ray floret color of plants of the cultivar Charm.
4. Plants of the new Chrysanthemum have more ray and disc florets per inflorescence than plants of the cultivar Charm.
5. Disc florets of plants of the new Chrysanthemum are shorter than disc florets of plants of the cultivar Charm.

A detailed comparison of plants of the new Chrysanthemum and the cultivar Charm appears in Chart B at the end of the specification.

The accompanying colored photograph illustrates the overall appearance of the new cultivar, showing the colors as true as it is reasonably possible to obtain in colored reproductions of this type. The photograph comprises a top perspective view of a typical flowering 16.5-cm container of Dark Fashion Time with five cuttings in the container and the terminal inflorescences removed (center-budded pot chrysanthemum). The ray floret and foliage colors in the photograph may appear different than the actual colors due to light reflectance.

In the following description, color references are made to The Royal Horticultural Society Colour Chart except where general terms of ordinary dictionary significance are used. The following observations and measurements describe plants grown in Oxnard, Calif. under commercial practice in a glass-covered greenhouse with average night temperatures of 18C, average day temperatures of 30C, and light levels of 2,000 (cloudy conditions) to 9,000 (sunny conditions) foot-candles.

After sticking unrooted cuttings of the new cultivar, plants received 21 long day/short nights followed by short day/long nights until flowering. Two weeks after the start of the short day/long night treatment, plants received four weekly spray applications of daminozide growth retardant at a rate of 2,500 ppm. Measurements and numerical values represent ranges or averages for six typical flowering plants.

Botanical classification: *Dendranthema grandiflora* cultivar Dark Fashion Time.

Commercial classification: Decorative potted Chrysanthemum.

Parentage: Spontaneous mutation of *Dendranthema grandiflora* cultivar Fashion Time (U.S. Plant patent application Ser. No. 08/627,606).

Propagation:

*Type.*—Terminal tip cuttings.

*Time to rooting.*—7 to 10 days with soil temperatures of 21C.

*Rooting habit.*—Fine, fibrous and well-branched.

Plant description:

*Appearance.*—Perennial herbaceous decorative potted plant. Stems upright, uniform habit and freely branching. Vigorous growth habit.

*Plant height.*—About 29 cm.

*Lateral branch length.*—22 to 23.5 cm.

*Quantity of lateral branches after removal of apical meristem.*—About 3.5.

*Stem color.*—147B.

*Foliage description.*—Number of leaves per lateral branch: About 16. Leaf arrangement: Alternate. Leaf size, fully expanded: Length: 10.5 to 11.5 cm. Width: 6 to 7 cm. Leaf apex: Acuminate. Leaf base: Attenuate. Leaf margin: Palmately lobed. Leaf texture: Upper and under surfaces slightly pubescent, smooth and dull. Veins prominent on under surface. Petiole length: About 2 cm. Color: Young foliage upper surface: 147A. Young foliage under surface: 147B. Fully expanded foliage upper surface: 147A. Fully expanded foliage under surface: 147B. Venation upper surface: 147B. Venation under surface: 147B. Petiole: 147A.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to 2 to 3 weeks of long day/short night conditions after sticking followed by photoinductive short day/long night conditions, flower about 55 to 57 days later.

*Postproduction longevity.*—In an interior environment, inflorescences and foliage of flowering plants will maintain good color and substance for at least 18 days.

*quantity of inflorescences.*—6 to 7 inflorescences per flowering stem.

*Inflorescence size.*—Diameter: About 9 to 10 cm. Depth (height): About 3.1 cm. Diameter of disc: 4 to 5 mm.

*Ray florets.*—Shape: Long, broad. Size: Length: 4 to 4.5 cm. Width: 1.5 to 1.7 cm. Apex: Rounded. Base: Acute. Margin: Entire. Texture: Satiny, smooth and glabrous. Aspect: Flat. Number of ray florets per inflorescence: About 330. Color: When opening, upper surface: 75A. When opening, under surface: 75A. Mature, upper surface: 75B, fading to 75D with subsequent development. Mature, under surface: 75D.

*Disc florets.*—Shape: Tubular. Size: Length: About 4 mm. Width: About 1 mm. Number of disc florets per inflorescence: About 27. Color: Immature: 154A. Mature: 12A.

*Peduncle.*—Aspect: Strong and angled about 45° to the stem. Length: 5.5 to 7 cm. Texture: Glabrous. Color: 147B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

CHART A

| CHARACTERISTIC | DARK FASHION TIME | FASHION TIME |
|---|---|---|
| RAY FLORET COLOR, WHEN OPENING, UPPER SIDE | 75A | 62B |
| RAY FLORET COLOR, MATURE, UPPER SIDE | 75B | 62C |
| RAY FLORET COLOR, MATURE, UNDER SIDE | 75D | 62D |
| RAY FLORET COLOR, MATURE, FADING TO | 75D | 155D |

CHART B

| CHARACTERISTIC | DARK FASHION TIME | CHARM |
|---|---|---|
| PLANT HEIGHT | 29 cm | 24 to 25 cm |
| QUANTITY OF LATERAL BRANCHES AFTER REMOVAL OF TERMINAL APEX | About 3.5 | About 3 |
| VIGOR | Vigorous | Moderate |
| RAY FLORET COLOR, WHEN OPENING, UPPER SIDE | 75A | 75B |
| RAY FLORET COLOR, WHEN OPENING, UNDER SIDE | 75B | 75C |
| NUMBER OF RAY FLORETS PER INFLORESCENCE | About 330 | About 200 |
| DISC FLORET LENGTH | About 4 mm | About 6 mm |
| DISC FLORET QUANTITY PER INFLORESCENCE | About 27 | About 7 |
| DIAMETER OF DISC | 4 to 5 mm | 2 mm |
| PEDUNCLE LENGTH | 5.5 to 7 cm | 4 to 4.5 cm |

It is claimed:

1. A new and distinct cultivar of Chrysanthemum plant named Dark Fashion Time, as illustrated and described.

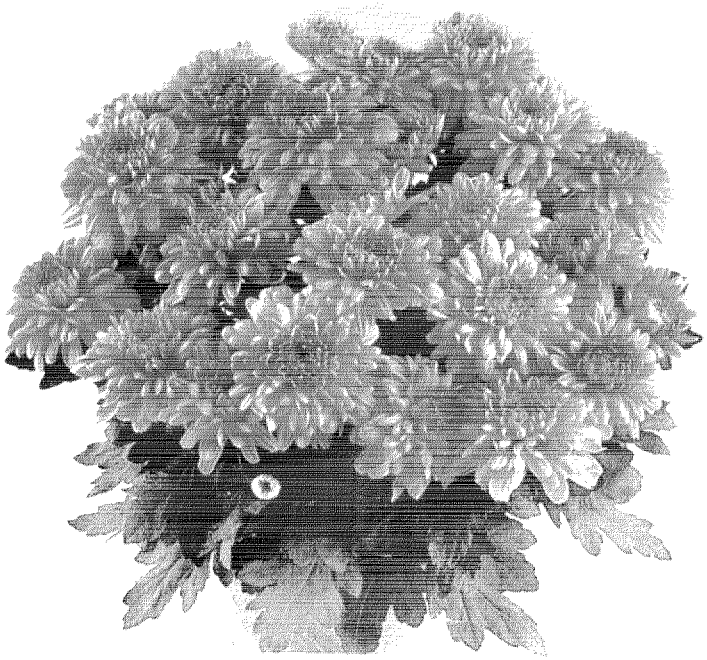

* * * * *